United States Patent [19]

Reti

[11] 4,200,095
[45] Apr. 29, 1980

[54] ARRANGEMENT FOR INTRAVENOUS ADMINISTRATION OR THE LIKE

[75] Inventor: Adrian R. Reti, Cambridge, Mass.

[73] Assignee: Millipore Corporation, Bedford, Mass.

[21] Appl. No.: 824,908

[22] Filed: Aug. 15, 1977

[51] Int. Cl.$^2$ .............................................. A61M 5/14
[52] U.S. Cl. ............................ 128/214 C; 128/214.2
[58] Field of Search ............... 128/214 R, 214 C, 276, 128/278, 214.2, 227; 55/159, 318; 222/145

[56] References Cited

U.S. PATENT DOCUMENTS

| | | | |
|---|---|---|---|
| 3,778,971 | 12/1973 | Granger et al. | 128/214 R |
| 3,854,907 | 12/1974 | Rising | 128/214 R |
| 3,886,932 | 6/1975 | Bobo et al. | 128/214 R |
| 3,896,733 | 7/1975 | Rosenberg | 128/276 X |
| 3,970,084 | 7/1976 | Raines | 128/214 C |
| 3,978,857 | 9/1976 | McPhee | 128/214 R |
| 3,982,534 | 9/1976 | Buckman | 128/214 C |
| 3,993,066 | 11/1976 | Virag | 128/214 C |
| 4,004,587 | 1/1977 | Jess | 128/214 R |
| 4,013,072 | 3/1977 | Jess | 128/214 C |
| 4,116,646 | 9/1978 | Edwards | 128/214 X |

*Primary Examiner*—Stephen C. Pellegrino
*Attorney, Agent, or Firm*—Irons and Sears

[57] ABSTRACT

The arrangement comprises a passageway for receiving liquid for intravenous administration (IV) or the like. A hydrophilic microporous membrane having a first pore size is disposed in the passageway at a first point so that all liquid passes through the microporous membrane at said first point. A microporous filter is disposed below the membrane in the passageway to filter all liquid passing through the passageway at the second point. The membrane has a bubble point high enough to withstand the expected head of liquid below it (the gravity head of the IV set). Should liquid from the source as it proceeds through the passageway from the microporous membrane to the filter be exhausted, then when air or gas reaches the membrane the flow of liquid is stopped because the upper, microporous membrane acts as an automatic shut-off valve. Air does not pass through the wet hydrophilic microporous membrane as long as the pressure does not exceed its bubble point. Accordingly there is no danger of air arriving at or passing through the microporous membrane to air-lock the lower passageway. A bellows drip chamber may be arranged in the passageway immediately below the membrane and may act as a drip chamber.

A further embodiment comprises such a bellows drip chamber arranged in the passageway below and immediately adjacent the microporous membrane, and a branch in the passageway in the section between the drip chamber and the hydrophilic filter which is used for the application of a secondary or auxiliary solution. In such a case, if the source of the secondary solution is higher than the source of the primary solution, the secondary solution will be preferentially administered. There will be no back-flow because air or gas in the bellows or drip chamber trapped immediately below the membrane will act as an air lock and prevent the backward flow of liquid in the first passageway because air or gas cannot pass through the hydrophilic upper microporous membrane which is wet by the liquid above it.

25 Claims, 3 Drawing Figures

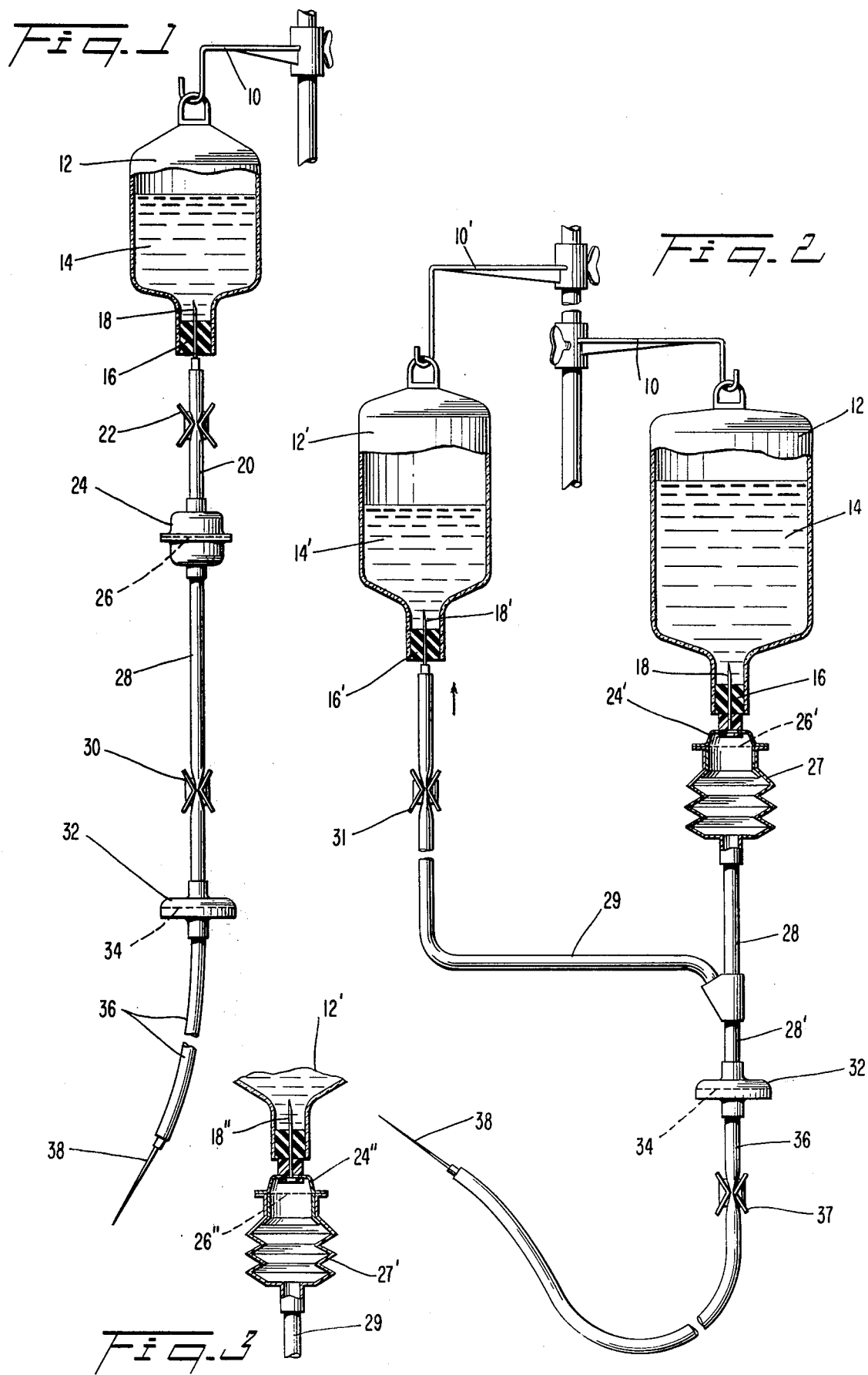

ARRANGEMENT FOR INTRAVENOUS ADMINISTRATION OR THE LIKE

BACKGROUND OF THE INVENTION

It is known to use a hydrophilic filter to filter liquid as it flows in a passageway for intravenous administration or the like. There is always a problem of gas or air intrained in the liquid reaching the filter and air locking it impeding further flow. One of the ways in which this problem has been attacked is to insert in a filter chamber holding the hydrophilic filter a hydrophobic membrane to vent air or gas that may collect in the filter chamber, the gas-free liquid then passing through the hydrophilic filter. There is, nevertheless, a possibility that the hydrophobic membrane, being fragile, may rupture and cause contamination of the liquid, or if the patient's venous pressure at the administration site is low enough, that air may be driven into the system through the hydrophobic vent. This air may then be accidentally infused into the patient's circulatory system.

Various arrangements have been proposed for the application of a secondary or "piggyback" solution higher than the primary solution, to be preferentially administered to the patient. Such arrangements usually involve a branch from the passageway through which liquid is provided from the principal or main solution. The branch leads to a piggyback solution. It has also been proposed to employ various valves or the like to assure the preferential administration of the secondary solution until exhaustion whereupon the flow of the primary solution takes up or begins again. The following patents may be considered as exemplary: U.S. Pat. No. 3,886,937 of June 3, 1975 to Bobo, et al; U.S. Pat. No. 3,982,534 of Sept. 28, 1976 to Buckman; and U.S. Pat. No. 3,993,066 of Nov. 23, 1976 to Virag. Note also the U.S. Pat. No. 3,854,907 of Dec. 17, 1974 to Rising. A prior art patent which exemplifies the venting of air or gas through a hydrophobic filter from a liquid being filtered for a patient is the above-identified Rising patent. Note also U.S. Pat. No. 4,013,072 to Jess. Prior patents which exemplify mechanical valving for administration of so-called "piggyback" solutions are U.S. Pat. No. 3,886,937 issued June 3, 1975 to Bobo, et al, and U.S. Pat. No. 3,982,534 issued Sept. 28, 1976 to Buckman, the latter also having means for removing air bubbles from the flow of liquid, and U.S. Pat. No. 3,993,066 issued Nov. 23, 1976 to Virag.

SUMMARY OF THE INVENTION

According to the invention, an arrangement for the intravenous administration of liquid from a source comprises a liquid passageway, which may be exemplified by polyvinyl chloride tubing and which in operation has an orientation for the gravitational flow of liquid through the passageway. A hydrophilic microporous membrane is disposed at a point in the passageway so that all of the liquid passing through the passageway at that point passes through the membrane. By such a membrane, for this purpose, is meant any structure which has the requisite uniformity of pore size to afford a defined bubble point. Such a membrane may be similar to those used for microporous filters. It is important from a production standpoint that membranes made for the purpose have a known controllable and predictable bubble point, so that if made in quantity none has a bubble point too large or too small. The bubble point of the membrane should exceed any pressure arising from the head of liquid at its expected location above the patient. The bubble point should also be sufficiently low to afford an ease of pumping action in priming the line as hereinafter described. A bubble point of between about 2 psi and 5 psi for the membrane is recommended.

A resilient walled chamber may be arranged in the passageway immediately below the membrane and may act also as a drip chamber. A hydrophilic microporous filter is disposed in the passageway to filter all the liquid passing through the passageway at a lower point than the membrane.

In operation a liquid for intravenous administration is supplied from a suitable source, such as a container or bottle to the passageway from above the membrane. The passageway leading to the patient is first filled with liquid which may be conveniently and easily accomplished using the resilient wall to introduce and pump liquid in a fashion described in detail hererinafter. Administration of the liquid may then begin. A small amount of air remains in the drip chamber below the membrane. If the source fails, i.e. the container empties, all the liquid will drain through the upper, coarse membrane. Nevertheless no air can intrude into the liquid column downstream of the microporous membrane because the bubble point of the upper, wet microporous structure is not exceeded. No further air or gas can accumulate in the column between the two filters, in a fashion to be trapped and carried to the lower filter to air lock the filter. Consequently even if hereinafter. container is replaced, the lower line remains emptied of air or gas, and replacement of the liquid container is simplified without danger to the patient.

If it is desired to administer liquid from a piggyback solution, the passageway may include a branch and a chamber, say a drip chamber, between the branch and the microporous membrane, as heretofore mentioned. A second passageway connected to the branch may lead to a second source, the piggyback solution container, which, if the piggyback solution is to be preferentially administered should be higher than the container for the primary solution. As stated above, some air remains in the chamber under the microporous membrane, as is usual for a drip chamber. Under these conditions the piggyback solution will be preferentially administered as long as the level of liquid from the piggyback container is higher than the level of the primary liquid. Backflow from the branch through the first passageway is prevented because the air cannot flow from the drip chamber through the wet microporous Such backflow is prevented by the air lock, from the air allowed to remain in the drip chamber, as the air cannot pass through the wet microporous membrane as long as the back pressure does not exceed the bubble point of this membrane. Consequently the preferential flow is maintained. As soon as the level of liquid from the piggyback solution falls to a point below the level of liquid from the primary container, or if flow from the piggyback solution is blocked, the flow from the primary container automatically is resumed.

BRIEF DESCRIPTION OF THE DRAWINGS

The various objects, advantages and novel features of the invention will be more fully apparent from the following detailed description when read in connection with the accompanying drawings in which:

FIG. 1 is a front view, largely schematic of a first embodiment of the invention, FIG. 2 is a front view, largely schematic, of an embodiment of the invention for administration of a piggyback solution, and FIG. 3 is a partial view, illustrating a modification of the embodiment of FIG. 2.

DETAILED DESCRIPTION

Referring to FIG. 1, a support bar 10 supports an inverted container 12 carrying a liquid 14 for intravenous infusion. The container 12 may be a bottle stoppered by a rubber stopper 16 through which is inserted a spike 18 leading to a polyvinyl chloride tubing 20 and from tubing 20 to a holder 24 carrying a microporous hydrophilic membrane 26. The spike may have a means (not shown) of admitting air to replace liquid out-flow, as a Cutter's standard spike which has a check valve, or the container 12 may be collapsible. The section of tubing 20 is held by a clamp 22 for selectively clamping off liquid flow and leads to the holder 24. The holder 24 may be a conventional filter holder carrying the microporous hydrophilic membrane 26. The outlet of the holder 24 leads in turn to a further section of polyvinyl chloride tubing 28. The tubing section 28 carries a clamp 30 for selectively clamping off flow. The tubing section 28 in turn leads to another filter holder 32 in which is mounted a microporous hydrophilic filter 34. The filter holder 32 is connected to a further tubing section 36 which leads to a cannula 38 suitable for insertion into a patient's vein.

By way of example, upper membrane 26 may have a pore size of about 5 microns to provide a bubble point of, say, between 2 and 5 psi, and the lower filter preferably has a pore size filtering against entry of microbial or bacterial invasion, for example a pore size of 0.22 microns. It is recommended that the bubble point of the membrane 26, be greater than about two psi, and preferably less than about five psi. The upper, latter limit is desirable so that air may be forced readily and easily through the membrane, by squeezing the flexible walls, as described more fully hereinafter. The lower limit is desirable so that there is a relatively low resistance to liquid flow, so that the liquid will flow through the membrane with sufficient freedom but still with a bubble point sufficient to withstand the head of the liquid column within the administration set. Generally the exposed surface of the membrane may be less than that of the finer pore, downstream filter 34. The tubings 20, 28 and 36 of FIG. 1 with the interposed filters constitute a passageway which in operation is oriented for the gravitational flow of liquid through the passageway, first through the upper membrane 26 and then through the section 28 and through the lower filter 34. The holders 24 and 32 are such that at the points in which the respective membrane and filter are disposed any liquid flowing through the passageway must flow through them. The upper filter holder 24 may comprise immediately below the membrane 26 a bellows chamber (not illustrated) as described in connection with FIG. 2. Otherwise, preferably, holder 24 of FIG. 1 has resilient walls immediately below the filter membrane 26 thereby to act as a bellows, but need not have accordion-like walls, such illustration (as in FIG. 2) being only a conventionalized showing in the drawing.

In operation the spike 18 is first entered into the stopper 16. The liquid is allowed to flow through the passageway formed by the sections of tubings 20, 28 and 36 and the filter holders 24 and 32, until liquid flows from the cannula 38. To accomplish the initial flow of liquid, with clamp 30 applied, the resilient walls of holder 26 may be squeezed, forcing air into the container 12. When the resilient walls are relaxed, the differential pressures will force liquid against the filter membrane and the flow of liquid through this membrane. Clamp 30 may now be relaxed and the pumping action may be repeated. When the resilient walls below the membrane is squeezed, liquid is forced downward, because air left in the chamber is prevented by the wet membrane from passing through it. Thus liquid is forced down through the passageway. When the wall is relaxed, liquid flows through the membrane to fill the increased volume. This repeated pumping action is continued until excess liquid flows from the cannula and all air is expelled from the passageway sections 28 and 36. A slight amount of air remains in holder 24, but above the tubing section 28 and in the chamber just below membrane 26. The tubing from the holder 32 to the tip of the cannula must be free of air. The cannula may then be inserted in the patient's vein and administration begun.

The upper membrane functions as an automatic shut-off valve when the supply bottle liquid 14 is emptied. The liquid below the upper membrane 26 can fall only far enough to reach equilibrium with the partial vacuum created below the membrane 26. The bubble point of the membrane exceeds the hydraulic head at its location. Therefore the liquid downstream of the membrane is prevented from completely flowing out. The downstream filter and line thus never receive air and cannot be air locked. If a new bottle is to be inserted into the system, flow can be commenced immediately. It is only necessary to withdraw the spike 18, hang a new bottle in place and insert the spike into the new bottle. Even if air has reached membrane 26 and flow has stopped, it is simple and convenient to replace the bottle. The spike may be withdrawn and inserted into a newly mounted bottle, and flow will begin again without danger of any air gaining access to the line below the holder 24. By using the membrane 26 having a relatively low bubble point (say between 2 and 5 psi) resumption of flow is facilitated and use of the clamp is not necessary. Further, it is easier to initiate flow through the filter having such a relatively low bubble point when initially "priming" the arrangement, than it would be through a finer membrane.

Referring now to FIG. 2, a holder 10 supports an inverted bottle or container 12 carrying the liquid 14 as in FIG. 1. In the arrangement of FIG. 2, however, the spike 18 leads directly to a holder 24' carrying microporous hydrophylic membrane 26'. Membrane 26' may have a pore size of five microns. Below and immediately adjacent the membrane holder 24' and preferably integral with this holder is a drip chamber 27 preferably bellows or flexible, which thence leads to a section of tubing 28, 28'. A second piggyback set may be connected from the section 28, 28' by means of a Y connector, the upper section 28 being one arm of the Y the lower section 28' leading from the leg of the Y and the tubing 29 from the piggyback constituting the other arm of the Y. The tubing 29 carries a clamp 31 and leads to a spike 18' inserted into the is a 16' of a secondary or so-called piggyback solution 14' carried in a container 12' on a support 10'. As frequently customary for piggyback containers, the container 12' is hung at a substantially higher level than the container 12, as indicated schematically by the break in the section 29 and by the arrows. As in the arrangement of FIG. 1, the microporous hydrophylic filter 34 of FIG. 2 may have a pore size of 0.22 microns.

In preparing the system for operation, assume that the clamps 31 and 37 are applied and spikes 18 and 18' not yet inserted. The spike 18 is inserted into the stopper 16 and the drip chamber bellows (which may be exemplified by a simple, resilient, transparent section of tubing) is pumped once manually. Air is forced up through spike 18. As the bellows returns to its relaxed position, it creates a vacuum in the drip chamber which tends to hasten flow of liquid and the wetting of the membrane 26 some liquid passing into the drip chamber. Then the clamp 37 is relaxed and the bellows compressed repeatedly. As the membrane 26' is wet, liquid is pumped during this step to fill tubing section 36 beyond clamp 37. The pumping may be repeated until air is expelled from sections 28 and 36 to the cannula. The cannula may then be inserted into the patient. The system is then locked against further air entry into the passageway section 28. Flow from the secondary solution bottle 12' through the branch passageway 29 thence through passageway section 28' toward the patient may be started or stopped at will by relaxing or impressing pressure from the clamp 31 on the section 29. The carrying solution 14 may be readily renewed by removing the container 12 and replacing it with another, simply withdrawing the spike 16 and reinserting it in the fresh container. This is an important and useful feature, saving time and simplifying renewal of the solution.

Before inserting the spike 18' air may be expelled from the remainder of the branch passageway or tubing 29. This may be done by connecting cannula 38 to the Y site and relaxing clamp 31 while clamp 37 is closed before the spike 18' is not inserted i.e. is free. The spike 18' may then be held at a low level, below container 12, until liquid expells all the air from section 29 and from the spike 18'. Then the spike 18' may be inserted through the stopper 16'.

When the clamps 31 and 37 are now relaxed, the piggyback solution, being at a higher level, will flow to the patient preferentially to the primary solution 14. The pressure differential created by the different liquid levels is exerted against the trapped air or gas in the bellows chamber which cannot pass through the membrane 26'. An air lock is thus formed because the back pressure does not exceed the bubble point of the wet membrane. Thus backflow is prevented. If the flow of the piggyback solution is to be stopped, that may be done by simply applying the pressure from the clamp 31 to close off the passageway or tubing 29 whereupon flow from the primary solution 14 through the primary passageway comprising holder 24', bellows drip chamber 27, sections 28 and 28', holder 32 and section 36, resumes.

If the piggyback solution 14' reaches to or below the level of the primary solution 14, the latter will commence flowing, and the solutions will flow jointly. Normally at this point, a nurse removes the piggyback set, or replaces it.

However, it may be preferable to supply a filter holder and a membrane at the spike 18' of the piggyback solution such as holder 24. Alternatively and preferably, as illustrated in the partial view of FIG. 3 a holder 24" like holder 24', with a membrane 26" like membrane 26' (and particularly having a similar bubble point characteristic), may be desirable for the piggyback solution. Such an arrangement also allows monitoring the flow of the piggyback solution. Moreover, in such case the flow of the piggyback solution will cease, because of the bubble point of the wet membrane 26", when the piggyback solution is exhausted and reaches the membrane 26" thus supplied. In initiating operation with a holder such as 24", similar considerations apply as those with respect to holder 24', namely all air should be carefully expelled from the tubing between the holder 24" and the filter 34, except for the small accumulation in the holder itself. Advantages similar to those for the similar arrangement with the primary solution are gained. A single compression of the bellows 27' may be used to hasten wetting of membrane 26" and the flow of the piggyback solution. Replacement of the solution is also simplified, as the spike 18" need only be inserted into the replacement container stopper even if the container 12" has previously been exhausted.

In any of these arrangements it is clear that if operation is properly initiated, air or gas cannot be entrained to be trapped in the tubing section below the first filter holder. Such air or gas usually cannot rise in such tubing section to escape because the usual small diameter of the tubing prevents such rise. A substantial advantage of the various embodiments disclosed herein is that replacement of containers of solution is facilitated and is readily accomplished by the nurse or attendant. No withdrawal and reinsertion of the cannula is required, even if the container has emptied. In view of the foregoing description it will be apparent that there is disclosed a novel and superior arrangement particularly suitable for the administration of intravenous solutions.

What is claimed is:

1. An arrangement for the intravenous administration of liquid comprising:
   a liquid passageway means,
   a hydrophilic membrane having a bubble point and disposed in said passageway means,
   a hydrophilic filter having a pore size finer than that of said membrane and disposed in said passageway means,
   in operation said membrane being disposed above said filter, thereby to define an intermediate passageway means section between them,
   whereby air passage through said membrane when wet is blocked and the replacement of a liquid supply for the administration is facilitated.

2. An arrangement as claimed in claim 1, said bubble point exceeding the expected hydraulic head at its point of disposition in said passageway means.

3. An arrangement as claimed in claim 2, said membrane having a pore size to have a bubble point between 2 and 5 psi, thereby to ease initiation of operation.

4. An arrangement for the intravenous administration of liquid, comprising:
   a liquid passageway means having in operation an orientation for the gravitational flow of liquid therein,
   a microporous membrane having a bubble point not less than 2 psi and disposed in said passageway means to receive and through which passes all liquid passing through said passageway means at the point of disposition of said membrane,
   a microporous filter having a pore size finer than that of said membrane, and disposed in said passageway means in such orientation at a lower point than said membrane to filter all liquid passing through said passageway means at said lower point, whereby air passage through said membrane when wet is blocked and the replacement of a supply for said liquid is facilitated.

5. An arrangement as claimed in claim 4, said bubble point exceeding the expected hydraulic head at said membrane.

6. An arrangement as claimed in claim 4 further comprising:
a branch in said passageway means between said membrane and said filter, and
a second liquid passageway means communicating with said first passageway at said branch.

7. An arrangement as claimed in claim 4, further comprising a drip chamber disposed in said passageway means below said membrane in said orientation, to receive all liquid flowing through said membrane, said membrane with gas in said chamber acting as an air lock against reverse flow of liquid from said branch.

8. An arrangement as claimed in claim 7, said drip chamber having resilient walls, to facilitate initiation of operation.

9. An arrangement as claimed in claim 5, further comprising a drip chamber disposed in said passageway means below and immediately adjacent said membrane, to receive all liquid flowing through said membrane, said chamber and said membrane affording an air lock against reverse liquid flow.

10. An arrangement for the intravenous administration of liquid from a source of liquid comprising:
a liquid passageway means having in operation an orientation for the gravitational flow of liquid therein and having means for connection to said source,
a first hydrophilic microporous membrane having a bubble point and disposed at a first point in said passageway means below said connection means in such orientation, said bubble point exceeding the expected hydraulic head at said membrane's point of disposition, said membrane being so arranged at said first point that the membrane receives and through it passes all liquid passing said first point,
a microporous hydrophilic filter having a pore size finer than that of said membrane and disposed in said passageway means in such orientation at a lower, second point than said membrane to filter all liquid passing through said passageway means at said lower point,
thereby to facilitate replacement of said source.

11. An arrangement as claimed in claim 10, said passageway means including a drip chamber between said branch and said membrane, air in said chamber in operation acting against said membrane to provide an air lock against reverse liquid flow.

12. An arrangement as claimed in claim 11, said drip chamber having transparent, resilient walls.

13. An arrangement as claimed in claim 12, said passageway means comprising polyvinyl chloride tubing.

14. An arrangement as claimed in claim 12, said drip chamber being immediately adjacent said membrane.

15. An arrangement as claimed in claim 11, said passageway means having a branch between said drip chamber and said filter.

16. An arrangement as claimed in claim 15, further comprising a second passageway means having one end connected at said branch to said first passageway means and having another end adapted for connection to a second source of liquid.

17. An arrangement as claimed in claim 16, both said passageway comprising polyvinyl chloride tubing.

18. An arrangement for the intravenous administration of liquid to facilitate replacement of a source of said liquid comprising:
a passageway means comprising a first section having means for connection to a source of liquid,
a first filter holder connected to said section to receive liquid therefrom,
hydrophilic microporous membrane held by said first holder to receive and through which passes all liquid passing through said first holder, said membrane having a bubble point exceeding the expected hydraulic head against it,
said passageway means comprising a second section connected to receive liquid from said first holder,
a second filter holder connected to said second section to receive liquid therefrom, and
a hydrophilic microporous filter having a pore size finer than that of said membrane and held by said second filter holder to filter all liquid passing through said second holder,
said passageway means comprising a third section to receive filtered liquid from said second filter.

19. An arrangement as claimed in claim 18, said first filter holder comprising a drip chamber immediately adjacent said membrane to receive liquid therefrom, and thus providing with said membrane during operation an air lock against reverse liquid flow.

20. An arrangement as claimed in claim 19, said bubble point being between 2 and 5 psi, to assure ease of initiation of operation.

21. An arrangement as claimed in claim 19, further comprising a branch passageway means connected to said second passageway means section.

22. An arrangement as claimed in claim 16, said second passageway means including a second hydrophilic microporous membrane having a pore size greater than that of said filter.

23. An arrangement as claimed in claim 16, said second passageway means including a second drip chamber immediately adjacent said second membrane to receive liquid therefrom.

24. An arrangement as claimed in claim 6, further comprising a hydrophilic microporous membrane in said second liquid passageway means and having a pore size greater than that of said filter.

25. An arrangement as claimed in claim 24, further comprising a drip chamber immediately adjacent said second membrane to receive liquid therefrom.

* * * * *